United States Patent [19]

Dering

[11] Patent Number: 5,642,528
[45] Date of Patent: Jul. 1, 1997

[54] PROTECTIVE FACE COVERING

[76] Inventor: Helen A. Dering, 18 Woodgreen Ct., Santa Rosa, Calif. 95409

[21] Appl. No.: 550,010

[22] Filed: Oct. 30, 1995

[51] Int. Cl.$^6$ ................................................. A42B 3/18
[52] U.S. Cl. ........................ 2/174; 2/9; 2/206; 132/319
[58] Field of Search ............................... 2/9, 172, 173, 2/174, 206, 207, 424; 132/319

[56] References Cited

U.S. PATENT DOCUMENTS

| | | | |
|---|---|---|---|
| 3,206,760 | 9/1965 | Santala | 2/9 |
| 3,317,921 | 5/1967 | Zarzour | 2/9 |
| 3,602,913 | 9/1971 | Neese | 2/9 |
| 3,828,366 | 8/1974 | Conrad et al. | 2/174 |
| 3,963,034 | 6/1976 | Runberg et al. | 132/9 |
| 4,428,079 | 1/1984 | McKee | 2/174 |
| 4,825,878 | 5/1989 | Kuntz et al. | 128/857 |
| 4,852,186 | 8/1989 | Landis | 2/9 |
| 4,864,653 | 9/1989 | Landis | 2/9 |
| 4,884,296 | 12/1989 | Nix, Jr. | 2/11 |
| 4,944,312 | 7/1990 | Smith | 128/857 |

*Primary Examiner*—Diana Biefeld

[57] ABSTRACT

A hair spray screen includes a semi-circular spring headband, a flexible transparent protective sheet extending downwardly from the headband, and a separate semi-circular spring neckband. To use, the headband is clipped around a user's forehead, so that the protective sheet is draped over the user's face and neck. The neckband is clipped around the neck over the sheet to secure the lower portion of the sheet. When worn, the hair spray screen protects the user from hair spray and other airborne substances commonly used at home and in beauty salons. It is easy to don and remove. It frees both hands of the user when worn, and it does not disturb the user's hairdo. It is also collapsible for transportation.

1 Claim, 1 Drawing Sheet

PROTECTIVE FACE COVERING

BACKGROUND OF THE INVENTION

1. Field of the Invention

This invention relates generally to face masks, specifically to a flexible transparent plastic screen for protecting a user's face, ears, and neck from hair spray.

2. Prior Art

People applying hair spray can easily get unwelcome, unpleasant, and sometimes harmful hair spray on their faces, hands, and into their eyes and ears. Therefore, many try to shield these areas with a hand, a towel, or other protective covering, and spray with the other hand. After spraying one half of the hairdo, they would switch hands to spray the other half. However, a hand is not large enough to make an effective shield. A larger, hand-held shield may also be ineffective, because it may not always be positioned correctly, especially when it must not block one's view.

Several proposed face masks or shields can be used for protecting a user's face from hair spray. U.S. Pat. Nos. 3,206,760 to Santala (1963); 3,317,921 to Zarzour (1964); 3,602,913 to Neese (1971); and 3,963,034 to Runberg et al. (1976) show rigid hair spray shields that are held up to a user's face with one hand. However, they are inconvenient because they must be held with one hand, so that a user may have to switch the shield and the spray can between the two hands to spray both halves of the hairdo. U.S. Pat. Nos. 4,428,079 to McKee (1984); 4,825,878 to Kuntz et al. (1989); 4,852,186 to Landis (1989); 4,864,653 to Landis (1989); 4,884,296 to Nix, Jr. (1989); and 4,944,312 to Smith (1990) show face masks or shields that are attached to the head with straps that completely encircle the head. However, the straps will substantially distort the hairdo, so that after hair spray is applied, the hair is fixed in the distorted shape.

OBJECTS OF THE INVENTION

Accordingly the primary object of the present invention is to provide a hair spray screen that protects a user's face, ears, and neck from hair spray.

Another object of the present invention is to provide a hair spray screen that frees both hands of the user.

Another object of the present invention is to provide a hair spray screen that does not disturb the user's hairdo.

Yet another object of the present invention is to provide a hair spray screen that is easy to don and remove.

Still another object of the present invention is to provide a hair spray screen that is collapsible for transportation.

Further objects of the present invention will become apparent from a consideration of the drawings and ensuing description.

SUMMARY OF THE INVENTION

A hair spray screen includes a semi-circular spring headband for being clipped around a user's forehead, a flexible transparent protective sheet extending downwardly from the headband to cover the user's face and neck, and a separate semi-circular spring neckband for securing a lower portion of the sheet to the user's neck.

Figure 1:
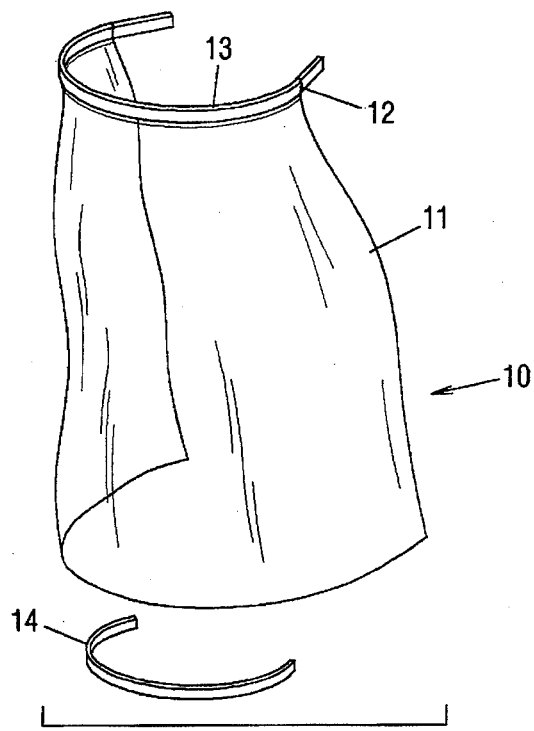
FIG. 1 is a front perspective view of a hair spray screen in accordance with a preferred embodiment of the invention.
Figure 2:
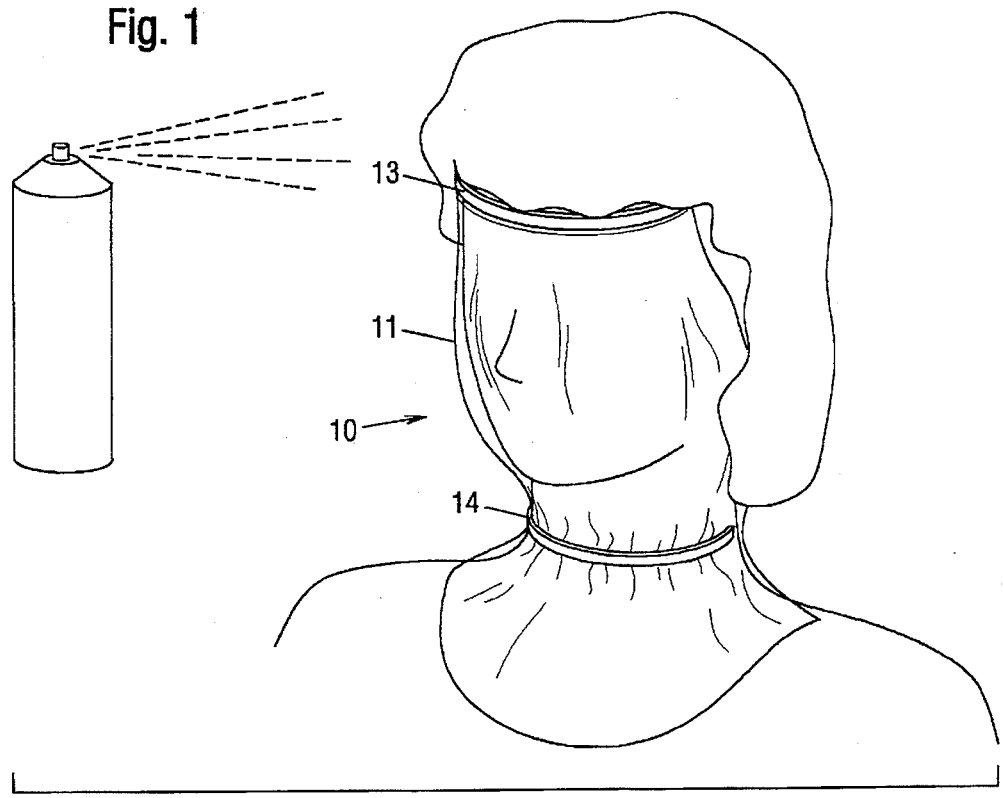
FIG. 2 is a front perspective view of the hair spray screen worn on a user.

| Drawing Reference Numerals | |
|---|---|
| 10. Hair Spray Screen | 11. Transparent Protective Sheet |
| 12. Hem | 13. Headband |
| 14. Neckband | |

DESCRIPTION—FIG. 1

In accordance with a preferred embodiment of the invention shown in the front perspective view in FIG. 1, a hair spray screen 10 includes a flexible transparent protective sheet 11, a hem 12 arranged along a top edge of sheet 11, a semi-circular spring headband 13 inserted through hem 12, and a separate neckband 14. Headband 13 and neckband 14 may be made of any suitable flexible material, including plastic and steel. Sheet 11 may be made of plastic or any other suitable material.

DESCRIPTION—FIG. 2

To use hair spray screen 10, headband 13 is clipped around a user's forehead, at the hairline, so that protective sheet 11 is draped over the user's face. The ends (not shown) of headband 13 are slipped under the hair on either side of the forehead. Protective sheet 11 is sized so that it substantially covers the exposed skin on the head, including the ears, and also the front and sides of the neck. Neckband 14 is worn around the neck over protective sheet 11 to secure the lower portion of the sheet.

Hair spray screen 10 thus protects the user's face, ears, and neck from hair spray and other liquid beauty products used at home and in beauty salons. It can also be used in a shower to protect the user's makeup. It does not completely encircle the head, so that it does not disturb the user's hairdo. Transparent protective sheet 11 allows a user to see what she is doing. Sheet 11 can be easily cleaned when soiled, so that hair spray screen 10 can be reused over and over again. Hair spray screen 10 is also simple enough to be produced and used as an inexpensive disposable item.

SUMMARY, RAMIFICATIONS AND SCOPE

Accordingly, I have provided a hair spray screen that protects a user's face, ears, and neck from hair spray and other airborne substances. It is easy to don and remove. It frees both hands of the user when worn. It does not disturb the user's hairdo, and it is collapsible for transportation.

Although the above descriptions are specific, they should not be considered as limitations on the scope of the invention, but only as examples of the embodiments. Many other ramifications and variations are possible within the teachings of the invention. For example, the protective sheet can be attached to the headband by being cemented or welded thereto. The neckband can be permanently attached to the sheet. Most of the sheet can be opaque or patterned, except for a transparent strip across the eyes. The sheet can include side extensions at its lower end for wrapping completely around the neck, or it can be extended down further to cover the shoulders. The sheet can be shaped to follow the contour of the face. The flexible sheet can be replaced with a less flexible but more durable panel. Therefore, the scope of the invention should be determined by the appended claims and their legal equivalents, not by the examples given.

I claim:

1. A flexible transparent contoured plastic face screen assembly for the protection of the face, ears and neck of a user from hair spray and other airborne substances, said plastic face screen assembly comprising:

(a) a semi-circular spring headband of plastic or metal composition for being slipped around a wearer's forehead at the wearer's hairline, (b) a flexible transparent rectangular sheet of plastic material extending downwardly from said headband substantially proportioned to cover a user's face, ears and neck without disturbing the hairdo of a user, (c) the face screen further including a hem arranged along a top edge of the sheet for insertion of said semi-circular spring headband, and (d) a separate unattached semi-circular spring neckband for securing a lower portion of said draped rectangular sheet around the neck of a user.

* * * * *